United States Patent
Corliss et al.

(10) Patent No.: US 6,919,146 B2
(45) Date of Patent: Jul. 19, 2005

(54) PLANAR RETICLE DESIGN/FABRICATION METHOD FOR RAPID INSPECTION AND CLEANING

(75) Inventors: Daniel A. Corliss, Hopewell Junction, NY (US); Christopher J. Progler, Plano, TX (US); Nakgeuon Seong, Wappingers Falls, NY (US)

(73) Assignee: International Business Machines Corporation, Armonk, NY (US)

(*) Notice: Subject to any disclaimer, the term of this patent is extended or adjusted under 35 U.S.C. 154(b) by 220 days.

(21) Appl. No.: 10/179,827

(22) Filed: Jun. 25, 2002

(65) Prior Publication Data

US 2003/0235764 A1 Dec. 25, 2003

(51) Int. Cl.[7] .............................. G03F 9/00; G03C 5/00
(52) U.S. Cl. ........................ 430/5; 430/311; 430/335; 430/950
(58) Field of Search .............................. 430/5, 311, 335, 430/950; 356/335, 239.3, 237.4; 134/2, 37

(56) References Cited

U.S. PATENT DOCUMENTS

| | | | |
|---|---|---|---|
| 5,780,187 A | | 7/1998 | Pierrat |
| 6,110,623 A | | 8/2000 | O'Grady et al. |
| 6,207,330 B1 | | 3/2001 | Balz et al. |
| 6,251,559 B1 | | 6/2001 | Huang et al. |
| 6,461,774 B1 | * | 10/2002 | Zimlich et al. ................. 430/5 |
| 6,682,861 B2 | * | 1/2004 | Chan ............................. 430/5 |
| 2002/0136966 A1 | * | 9/2002 | Shinagawa et al. ............ 430/5 |

* cited by examiner

Primary Examiner—Geraldine Letscher
(74) Attorney, Agent, or Firm—McGinn & Gibb, PLLC; Todd M. C. Li, Esq.

(57) ABSTRACT

A reticle has a transparent substrate, mask shapes on the substrate, a transparent material covering the mask shapes and an optional anti-reflective material over the transparent material.

20 Claims, 3 Drawing Sheets

PLANAR RETICLE DESIGN/FABRICATION METHOD FOR RAPID INSPECTION AND CLEANING

BACKGROUND OF THE INVENTION

1. Field of the Invention

The present invention generally relates to reticles used in photolithographic semiconductor manufacturing and more particularly to an improved reticle that includes a planar anti-reflective surface which is easily checked for foreign matter.

2. Description of the Related Art

Transparent pellicles are used to protect the surface of a reticle from the deposition of contaminants after it has been fabricated and while it is in use during the manufacture of semiconductor integrated circuits (for example, see U.S. Pat. No. 6,284,417, incorporated herein by reference). The requirement of a pellicle presents challenges to define new, cost effective materials for use at shorter imaging wavelengths. Currently, there are no known materials for use at 157 nm and shorter wavelengths, and at 193 nm pellicle durability is questionable. The ability to overcome this requirement, omit the pellicle and use a reticle without it, is precluded by the inability to rapidly and adequately inspect and remove deposited contaminants and ensure defect free integrated circuit imaging.

After a reticle has been fabricated and is in use in the manufacture of integrated circuits, there are two conventional methods that can be utilized to qualify the reticle as defect free. The first method is to perform a thru-the-reticle transmission and reflectance inspection test against a reticle design database, and/or identical reticle pattern within the same reticle or another reticle. The second method is to image a wafer with the reticle and inspect the wafer image against a reticle design database, and/or identical pattern within the same reticle pattern area or generated with another reticle.

The first method requires expensive equipment and very long inspection times. It provides sufficient contaminant detection capability and is currently used to initially qualify a reticle after it has been fabricated. However, it does not provide a timely or cost effective solution for a pellicle-less reticle operation, as the reticle would be required to be inspected very frequently. Possibly as often as every wafer. With wafer processing times on the order of 30 to 90 seconds per wafer, it is not cost effective to inspect a reticle for several hours between each wafer.

The second method has similar cost and time constraints. It is further inhibited by the low contrast of patterns on the wafer which limit defect detection sensitivity. This method also requires significant computer modeling to overcome the process induced changes (e.g., from chemical processing, lens aberrations, etc) when the reticle pattern is imaged onto a wafer. The additional loss of performance for inspection capability coupled with poor cost and lengthy inspection times result in an ineffective solution for pellicle-less operation of a reticle.

The use of other techniques within the exposure tool, such as grazing incidence (scattered light) inspection technology, are fast and cost effective, but are limited to large contaminants (much larger than the reticle design feature size) and are not able to qualify the conventional reticle as defect free. This is due to limits in the ability to distinguish between feature edges and contaminants, as well as not detecting contaminants in the recesses of the reticle topography. As a result, they do not represent a viable technique for pellicle-less operation with a conventional reticle. However, they are used very effectively, when inspecting conventional reticles, to capture contaminants that are deposited on a pellicle surface, due to the pellicle's flatness and its reflective nature to grazing incidence light.

When the conventional pellicle technique is not available (e.g., due to lack of acceptable materials of construction) or the pellicle solution is no longer cost effective as the wavelength of lithography source gets shorter, pellicle-less operation can be usable with cost effective particle detection and removal techniques provided.

Since pellicle-less reticles are likely for wavelengths at 157 nm and below, where currently there are no acceptable materials of construction or cost effective pellicle solutions, there is a need for an improved reticle structure that allows easy detection of foreign matter particles, without requiring a pellicle.

SUMMARY OF THE INVENTION

In view of the foregoing and other problems, disadvantages, and drawbacks of the conventional reticle structures the present invention has been devised, and it is an object of the present invention to provide a structure and method for an improved reticle structure having a planar anti-reflective surface.

In order to attain the object(s) suggested above, there is provided, according to one aspect of the invention a reticle having a transparent substrate, mask shapes on the substrate, a transparent material covering the mask shapes, and an optional anti-reflective material over the transparent material. The anti-reflective material is transparent to a first wavelength of light and reflective to a second wavelength of light. The first wavelength of light is used to expose a pattern of the mask shapes on a surface and the second wavelength of light is used to inspect the anti-reflective material. The anti-reflective material and the transparent material have a planar surface. The reticle is used in a photolithographic system to expose patterns on semiconductor wafers. The reticle also has a transparent substrate having mask shape trenches, an opaque material within the trenches, and an anti-reflective material over the substrate.

The invention also includes a method of exposing a pattern on a surface using a reticle having mask shapes covered by a planar anti-reflective material. The method includes loading the reticle in an exposure tool, directing a second wavelength of light on the anti-reflective material, observing whether the second wavelength light illuminates foreign matter on the anti-reflective material, cleaning the anti-reflective material if the observing process detects the foreign matter, and illuminating the reticle using a first wavelength light to expose a pattern of the opaque mask shapes on a surface. The observing and cleaning processes are performed without removing the reticle from the tool. The anti-reflective material is transparent to the first wavelength light and reflective to the second wavelength light. The cleaning process blows the foreign matter from the anti-reflective surface. The observing process includes determining a level of difficulty of removing the foreign matter. The level of difficulty determines whether the cleaning process will be performed with the reticle in the tool or with the reticle outside said tool.

The invention also includes a method of manufacturing the reticle that includes patterning mask shapes on a transparent substrate, depositing a transparent material over the mask shapes, planarizing the transparent material, and depositing an anti-reflective material over the transparent material. The process of patterning mask shape trenches within the transparent substrate includes depositing an opaque material over the substrate and within the trenches. Planarizing the substrate allows the opaque material to remain only within the trenches. The anti-reflective coating is optional since the planar surface by itself will also provide an acceptable inspection surface. The method planarizes the opaque or anti-reflective material.

BRIEF DESCRIPTION OF THE DRAWINGS

The foregoing and other objects, aspects and advantages will be better understood from the following detailed description of a preferred embodiment(s) of the invention with reference to the drawings, in which.

DETAILED DESCRIPTION OF PREFERRED EMBODIMENTS OF THE INVENTION

As mentioned above, conventional reticle structures have topography that limits their ability to be inspected with traditional grazing angle inspection technologies. This limitation results from the inability to adequately detect contamination that may propagate in the recesses of the reticle structure or differentiate between reticle pattern edges and contaminants. The inventive reticle structure provides a flat, highly reflective surface that is conducive to grazing inspection technology and will result in sufficient contrast for contaminant detection and subsequent removal. When pellicle-less reticle application is required, the structure of the inventive reticle allows the use of rapid and robust particle detection as well as facilitating ease in particle removal, subsequently ensuring defect free integrated circuit imaging.

Because the inventive reticle structure has a flat surface and high reflectivity to grazing incidence inspection light, the detection of particle can be done with simple scattering detection methods with high accuracy and relatively high speeds. Furthermore, the flat surface facilitates ease in particle removal with simple cleaning methods (e.g., ionized gas clean, CO2 mechanical clean, pressurized high purity glass clean, etc.).

Figure 1A:
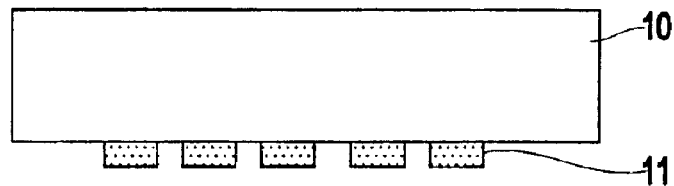
FIGS. 1A–1D are schematic diagrams showing one process to form the inventive reticle.
Figure 1B:
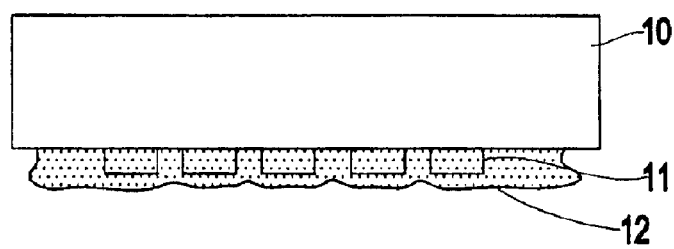

Referring now to the drawings, and more particularly to FIG. 1A, there is shown a reticle having chrome patterns 11 on a transparent substrate 10. The details of forming the structure shown in FIG. 1A are well known to those ordinarily skilled in the art and are not discussed herein so as not to obscure the salient features of the invention. A transparent material 12 is deposited over the mask shapes 11. The transparent material 12 can be any material that readily adheres to the substrate 10 and the masks 11. For example, the transparent material 12 could be an oxide layer deposited using a plasma enhanced chemical vapor deposition process (PE-CVD) or a liquid deposit/spin on oxide film. The transparent material 12 is deposited to have a thickness greater than the height of the mask structures 11. In other words, the transparent material 12 covers all the mask structures 11.

Figure 1C:
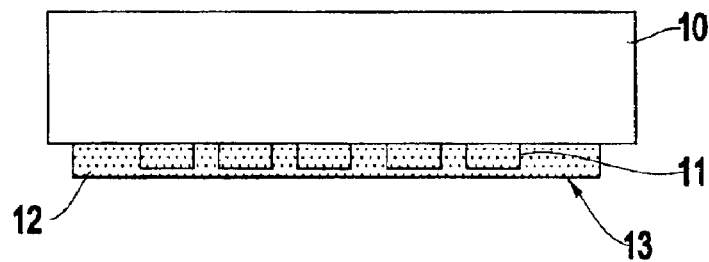

In FIG. 1C, the transparent material 12 is planarized forming a flat surface 13. The surface can be planarized using any conventional method such as chemical mechanical polishing (CMP), etch back processing, etc. At this point, the invention may be used as is, or to further enhance inspection sensitivities and/or more readily facilitate the cleaning process, or an optional anti-reflective layer may be added as described in the following steps. Next, in FIG. 1D, an anti-reflective layer 14 is deposited on the flat surface of the transparent material 12. The anti-reflective layer 12 is transparent to wavelengths of light used to expose the pattern of the mask structure 11. However, the anti-reflective layer 14 is reflective to a specific range of inspection wavelengths.

These reflective wavelengths are projected on to the anti-reflective layer 14 to determine whether foreign matter particles are present on the anti-reflective layer 14. Exposure wavelengths can be 193, 157, 126 and 13 nm, which are decided by lithographic light sources that the reticles are to be utilized with. Inspection wavelengths can be in the range of 230 nm to 650 nm, but an anti-reflectance material does not have to be reflective throughout the range of 230 nm to 650 nm. Optimum materials can be chosen by a combination of requirements of exposure wavelength and inspection wavelength. Examples of potential anti-reflective coating materials are magnesium fluoride and aluminum oxide multilayers.

Figure 2A:
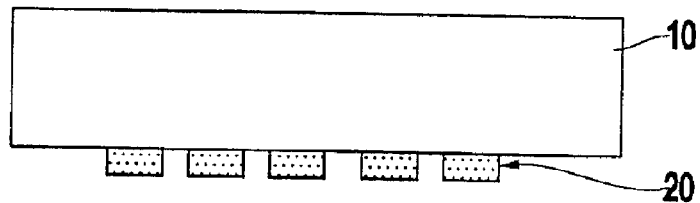
FIGS. 2A–2E are schematic diagrams showing another process to form another inventive reticle.
Figure 2B:
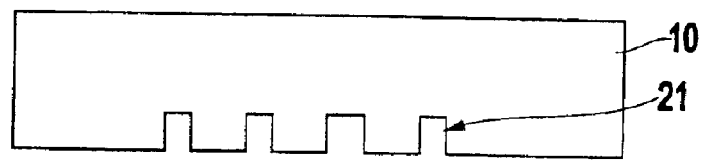

FIGS. 2A–2E illustrate another embodiment of the invention that utilizes opaque filled trenches. FIG. 2A illustrates an etching mask 20 that is formed on the surface of the transparent substrate 10 using conventional, well known processing such as photolithography. The substrate 10 is etched to form a pattern of trenches 21 and the mask 20 is removed, and shown FIG. 2B.

Figure 2C:
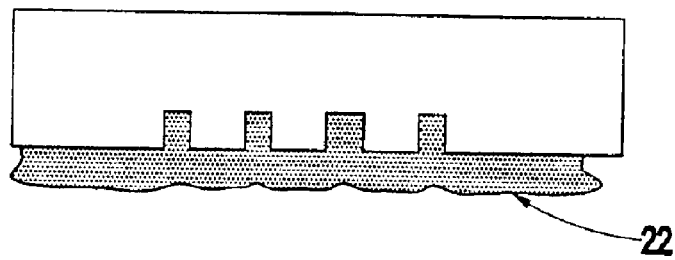
Figure 2D:
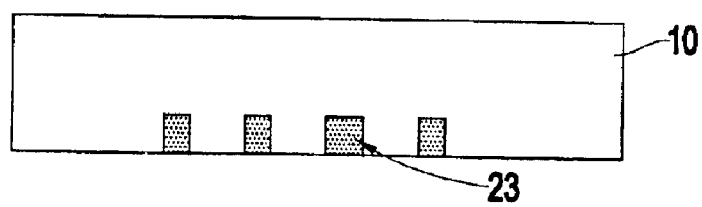
Figure 2E:
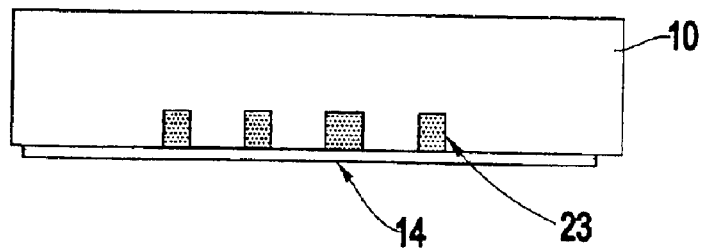

In FIG. 2C, in the opaque material 22 is deposited over the substrate. The opaque material 22 could be any material that will block light (for example, aluminum, tungsten, copper, Chrome 100, etc.). The structure is then planarized, and shown in FIG. 2D, to remove the opaque material 22 from all areas of the substrate 10 except the trenches 21. This processing leaves the trenches with a pattern of opaque structures 23. At this point, the invention may be used as is, or to further enhance inspection sensitivities and/or more readily facilitate the cleaning process, an optional anti-reflective layer may be added as described in the following steps. In FIG. 2E, the anti-reflective coating 14 is deposited over the substrate 10 and opaque structures 23.

As discussed above, there are two conventional methods that can be utilized to qualify the reticle as defect free. The first method is to perform a thru-the-reticle transmission and reflectance inspection test against a reticle design database, and/or identical reticle pattern within same reticle or another reticle. The second method is to image a wafer with the reticle and inspect the wafer image against a reticle design database, and/or identical pattern within same reticle pattern area or generated with another reticle. However, no conventional system allows the reticle to be examined quickly or while in the exposure tool.

Figure 1D:
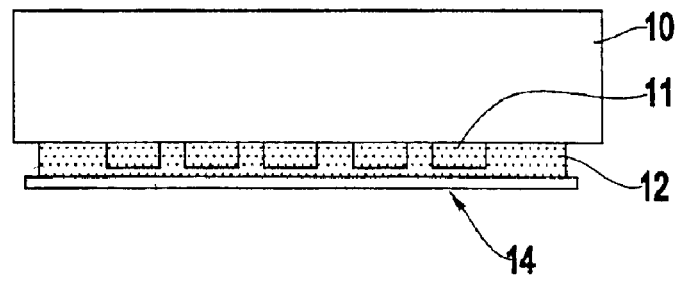

The planar anti-reflective surface 14 included within the inventive structures shown in FIGS. 1D and 2E allows the reticle to be quickly checked for foreign matter particles while it is positioned in the exposure tool. This allows the reticle to be checked before each processing run, thereby facilitating defect free reticle use in the fabrication of integrated circuits.

Figure 3:
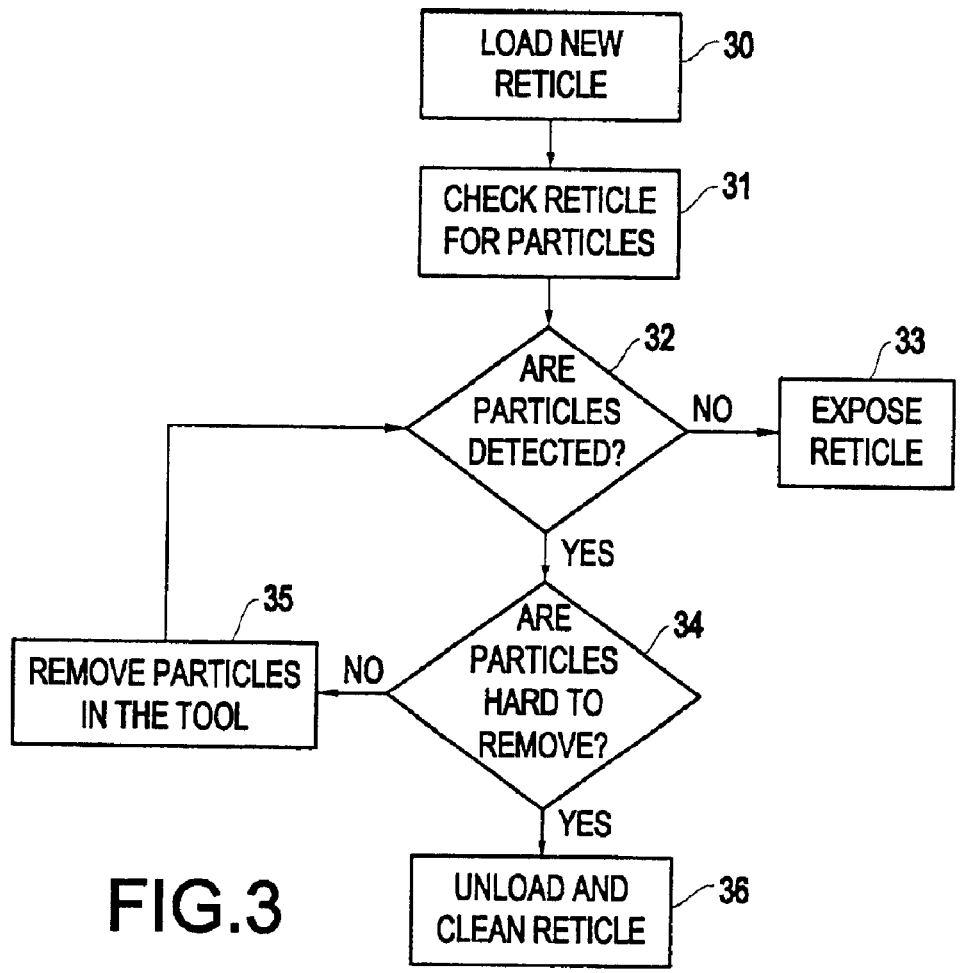
FIG. 3 is a flow diagram illustrating a preferred method inspecting and cleaning the inventive reticle according to the invention.

FIG. 3 shows the use of the inventive structure in flowchart form. In item 30, the reticle is loaded into the exposure apparatus. In item 31, an inspection light having a wavelength in the anti-reflective range of the anti-reflective material 14 (or planarized surface without the anti-reflective coating 12) is shown upon the anti-reflective material 14 (or planarized surface without the anti-reflective coating 12) to allow foreign matter particles to be observed. Particles are detected using any known detection scheme. For example, an oblique incident laser can be used to detect scattered light or a laser scanning confocal lens system can be used to detect particles at dark field illuminations.

In item 32, if the particles are not detected, the reticle is used to expose the pattern (item 33). If particles are detected, in item 34 the invention checks to determine whether particles are removable for given technique installed within the tool. If the process of removing the particles is below a certain threshold of difficulty, the invention removes particles from the reticle while it is still in place in the tool. For example, if the particles are readily removable, they can be blown off the reticle. However, if the particles are of the type that are to difficult to be blown off the surface, the reticle can be removed from the tool and cleaned in a separate processing environment, as shown in item 36. The degree of difficulty of removal can be categorized, and checked against a lookup table generated by accumulated data from repeated tool use, dependent upon the size of the particle, its material composition, as well as other known manufacturing variables.

Figure 4A:
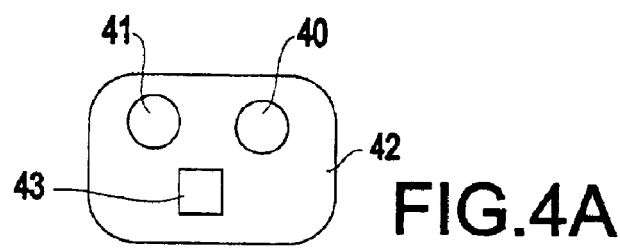
FIGS. 4A and 4B are schematic diagrams of an exposure tool.
Figure 4B:
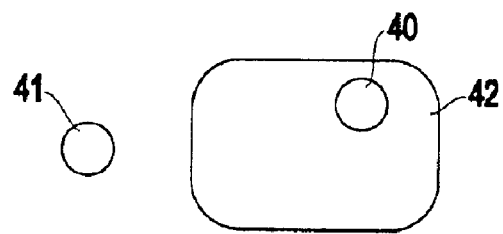

FIGS. 4A and 4B are schematic diagrams of an exposure tool 42. The particle detector 41 can be located inside the exposure tool 42, as shown in FIG. 4A, or outside the exposure tool 42, and shown in FIG. 4B. Item 40 represents the exposure apparatus (stepper/scanner and stepper/scanner controller) that expose the pattern on to a semiconductor wafer. Item 43 represents a cleaning mechanism (such as an air source) that can be used to blow particles off the reticle.

Therefore, as shown above, the invention provides new reticle structures that include a planar surface and/or planar anti-reflective surface that allows the reticle to be regularly checked for foreign matter particles and a system using the inventive structure for checking for foreign matter particles.

While the invention has been described in terms of preferred embodiments, those skilled in the art will recognize that the invention can be practiced with modification within the spirit and scope of the appended claims.

What is claimed is:

1. A reticle comprising:
   a transparent substrate;
   mask shapes on said substrate; and
   a planar transparent material covering said mask shapes and said substrate.

2. The reticle in claim 1, further comprising an anti-reflective material over said transparent material.

3. The reticle in claim 2, wherein said anti-reflective material is transparent to a first wavelength of light and reflective to a second wavelength of light.

4. The reticle in claim 3, wherein said first wavelength of light is used to expose a pattern of said mask shapes on a surface and said second wavelength of light is used to inspect said anti-reflective material.

5. The reticle in claim 2, wherein said anti-reflective material has a planar surface.

6. The reticle in claim 1, wherein said reticle is used in a photolithographic system to expose patterns on semiconductor wafers.

7. A reticle comprising:
   a transparent substrate having mask shape trenches; and
   an opaque material within said trenches,
   wherein said substrate and said opaque material form a planar surface.

8. The reticle in claim 7, further comprising an anti-reflective material over said planar surface.

9. The reticle in claim 8, wherein said anti-reflective material is transparent to a first wavelength of light and reflective to a second wavelength of light.

10. The reticle in claim 9, wherein said first wavelength of light is used to expose a pattern of said mask shape trenches on a surface and said second wavelength of light is used to inspect said anti-reflective material.

11. The reticle in claim 8, wherein said anti-reflective material has a planar surface.

12. The reticle in claim 7, wherein said reticle is used in a photolithographic system to expose patterns on semiconductor wafers.

13. A method of inspecting and cleaning a reticle having mask shapes and a substrate covered by a planar surface, said method comprising:
   loading said reticle in an exposure tool;
   directing light on said planar surface; and
   observing whether said light illuminates foreign matter on said planar surface.

14. The method in claim 13, further comprising:
   cleaning said planar surface if said observing process detects said foreign matter; and
   illuminating said reticle using a second light having a different wavelength then said light to expose a pattern of said mask shapes on an adjacent surface.

15. The method in claim 13, wherein said observing process is performed without removing said reticle from said tool.

16. The method in claim 14, wherein said cleaning process is performed without removing said reticle from said tool.

17. The method in claim 13, wherein said planar surface is transparent to said second light and reflective to light.

18. The method in claim 13, wherein said cleaning process comprises blowing said foreign matter from said planar surface.

19. The method in claim 13, wherein said observing process includes determining a level of difficulty of removing said foreign matter, and wherein said level of difficulty determines whether said cleaning process will be performed with said reticle in said tool or with said reticle outside said tool.

20. The method in claim 19, wherein said level of difficulty is determined by observing characteristics of said foreign matter, including size of foreign matter particles and material composition of foreign matter particles.

* * * * *